United States Patent [19]
Jobson

[11] Patent Number: 5,693,894
[45] Date of Patent: Dec. 2, 1997

[54] FLUID CONTROLLED ISOKINETIC FLUID SAMPLER

[75] Inventor: Harvey Eugene Jobson, Reston, Va.

[73] Assignee: The United States of America as represented by the Secretary of the Interior, Washington, D.C.

[21] Appl. No.: 571,645

[22] Filed: Dec. 13, 1995

[51] Int. Cl.⁶ .................................................. G01N 1/20
[52] U.S. Cl. .................................. 73/863.03; 73/864.34
[58] Field of Search ........................... 73/863.02, 863.03, 73/864.34, 864.35

[56] References Cited

U.S. PATENT DOCUMENTS

| | | | |
|---|---|---|---|
| 2,693,114 | 11/1954 | Topp et al. | 73/863.02 |
| 2,983,147 | 5/1961 | Morgan | 73/863.02 |
| 3,635,092 | 1/1972 | Maughon et al. | 73/864.02 |
| 3,719,081 | 3/1973 | Lynn et al. | 73/863.03 X |
| 4,606,233 | 8/1986 | Burney | 73/864.34 X |
| 5,437,201 | 8/1995 | Krueger | 73/864.35 |

*Primary Examiner*—Thomas P. Noland
*Attorney, Agent, or Firm*—E. Philip Koltos

[57] ABSTRACT

A sampler for obtaining an isokinetic sample of a flowing fluid. A liquid-filled, fluid-tight container has a deflated bag within it. The sampler is positioned within the flowing fluid stream, and the liquid is pumped from the container at a rate proportional to the flow rate of the flowing fluid to draw a sample of the fluid into the bag at the same rate as the flow rate of the flowing fluid. When the bag is filled it can be removed from the container and the container inlet tube replaced, allowing the sampler to be used for another sample without laborious cleaning in the field.

10 Claims, 2 Drawing Sheets

5,693,894

FLUID CONTROLLED ISOKINETIC FLUID SAMPLER

BACKGROUND OF THE INVENTION

The present invention is a fluid controlled isokinetic fluid sampler for obtaining a sample of a flowing fluid and material suspended therein from a flow stream to permit determination of the concentration of contaminants in the flow stream, such as sediment and other water quality constituents in the effluent from an industrial plant or in a river or stream. More particularly, the present invention is a sampler for obtaining a sample of a flowing fluid from a flow stream such as a river or the effluent of an industrial plant or a waste water treatment plant, with the sample entering the sampler at a flow rate equal to the flow rate of the flow stream so that the concentration of contaminants in the sample is representative of the concentration in the flow stream.

Samples of flowing fluids and material suspended therein, such as flowing water in a river or stream or the discharge water from an industrial plant or water treatment plant, are often desired for testing to determine the make up and quality of the flowing fluid. However, to provide meaningful test results, such samples must be representative of the flow stream. Further, it is necessary that the sampler not contaminate the sample.

Obtaining a representative sample can best be done isokinetically, that is without a change in the fluid speed or flow direction as fluid from the flow stream enters the sampler. Samples of flowing liquids which are collected in a non-isokinetic manner are frequently biased relative to the concentrations of material such as sediment suspended within the liquid. Sampling under isokinetic conditions also permits the sample to be flow weighted so that a single sample can be collected and analyzed to provide a measure of the amount of sediment passing a given cross section of the flow stream per unit time.

The desirability of obtaining isokinetic samples has been known for many years. Many early attempts to obtain isokinetic samples have involved pumping a sample of a flowing liquid to the surface of the flow stream with a pump having a pumping rate controlled electronically by a flow sensor. However, the pump components frequently are contaminated and so can contaminate the sample, with the result that the sample is not representative of the flow stream. Various non-pumping isokinetic sediment samplers have been developed, but most of these cannot be used at fluid depths greater than about 17 feet. Further, most of these samplers permit the sample to be contaminated as it is obtained.

In order to reduce such contamination, bag samplers have been developed, which can be operated at any depth. However, at a flow rate below about three feet per second, such bag samplers do not obtain samples isokinetically, since the dynamic pressure of the fluid entering the sampler is not sufficient to inflate the bag.

Isokinetic samplers have been developed for lower fluid velocities, but such samplers are initially filled with air. As a consequence, these samplers are limited to depths of operation of less than about 17 feet, and the rate of vertical descent during the placement of these samplers is very low. Further, the buoyancy of the air makes it necessary for such samplers to have a very heavy frame or other weighting system in order to provide stability.

An additional problem with many existing samplers is that the inflow of the fluid into the sampler cannot be started or stopped while the sampler is in the flow stream. As a consequence, such samplers cannot be utilized to obtain a point sample, i.e., a sample at a specific depth.

SUMMARY OF THE INVENTION

The present invention is a fluid sampler overcoming these deficiencies of the prior art. In accordance with the present invention, an inflatable bag is provided within a hollow fluid-tight housing which is filled with water or other appropriate liquid. An inlet tube permits a sample of a flowing fluid to be introduced into the inflatable bag from the exterior of the housing to inflate the bag within the housing. A pump is provided to pump the water from within the housing through an outlet tube to the exterior of the housing, and a control device responsive to the flow rate of the flowing fluid causes the pump to pump the water from within the housing through the outlet tube to the exterior of the housing at a flow rate proportional to the flow rate of the flowing fluid. As the water is pumped from within the sealed housing, a sample of the flowing fluid is drawn into the bag, inflating the bag to replace the water that is pumped from within the housing. The flow rate at which the pump exhausts the water from the container is based on the ratio of the diameter of the inlet tube and the outlet tube so that the sample is drawn through the inlet tube into the container with the same flow rate as the flowing stream, providing isokinetic sampling. Since the pump is not in the inlet to the inflatable bag, contamination of the sample by the pump is avoided. Since the housing is initially filled with water, the sampler is not buoyant, and so no stabilizing weight needs to be provided. Further, a solenoid valve keeps the outlet tube blocked until the sampler is positioned at the desired location, permitting point sampling.

BRIEF DESCRIPTION OF THE DRAWINGS

These and other aspects and advantages of the present invention are more apparent from the following detailed description and claims, particularly when considered in conjunction with the accompanying drawings. In the drawings:

DETAILED DESCRIPTION OF PREFERRED EMBODIMENTS

Figure 1:
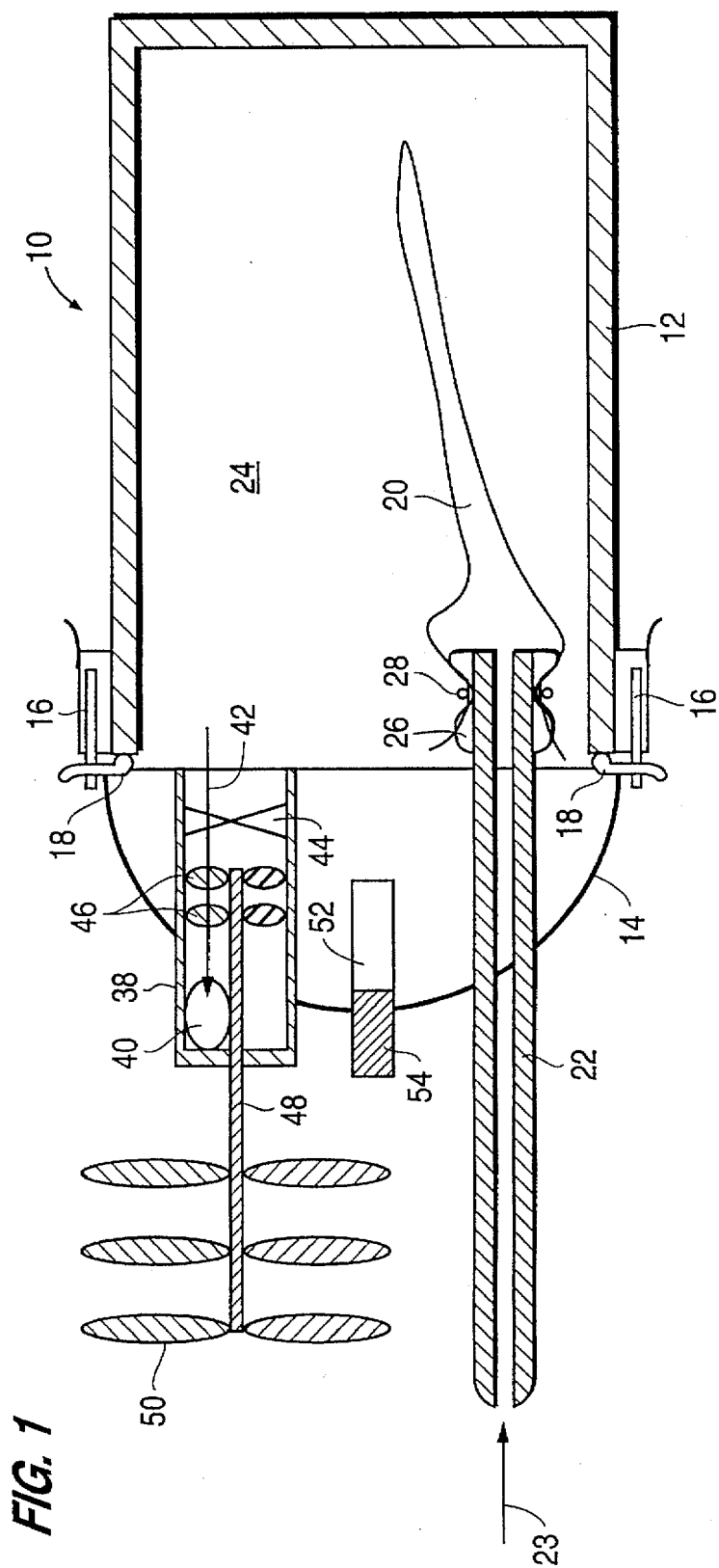
FIG. 1 is a schematic sectional view of a fluid controlled isokinetic fluid sampler in accordance with one embodiment of the present invention and is taken along line I—I of FIG. 2.
Figure 2:
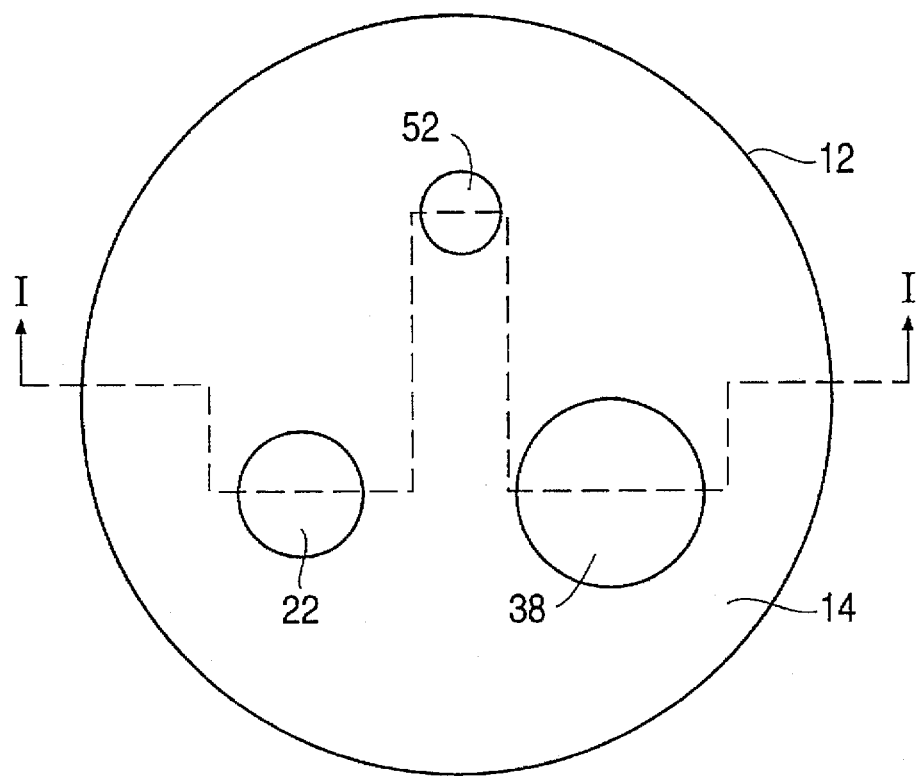
FIG. 2 is an end elevational view of the sampler of FIG. 1.

As depicted in FIG. 1, the fluid controlled isokinetic fluid sampler of the present invention includes a hollow closed housing 10 made up of a cylindrical container 12 and a cap 14. Cap 14 is securely fastened to container 12 by spring-loaded latches 16. Preferably, cap 14 is curved substantially as depicted in FIG. 1 for laminar diversion of the flowing fluid. An O-ring 18 assures that cap 14 is sealed to container 12 in a fluid tight manner so that container 12 and cap 14 define a closed chamber 24. An inlet tube 22 passes through cap 14, and a fluid impervious inflatable bag 20 is secured to the end of inlet tube 22 within chamber 24. A gasket 26 and a sealing device such as a rubber band 28 assure that inflatable bag 20 is securely fastened to the end of inlet tube 22 in a fluid tight manner.

An outlet tube 38 also passes through cap 14 and permits fluid flow from the interior of chamber 24 through outlet tube 38 and exhaust port 40, as indicated by arrow 42, to the exterior of sampler 10. Within outlet tube 38 a solenoid valve 44 is provided to permit cutoff of the outlet flow. Further, a pump 46 within outlet tube 38 is connected to a pump shaft 48 which passes through the closed outer end of outlet tube 38. A propeller 50 is provided on the outer end of pump shaft 48. Preferably, inlet tube 22 extends forward of cap 14 a greater distance than does outlet tube 38 so that the water discharged through exhaust port 48 does not contaminate the sample drawn into inlet tube 22. A filler tube 52 also passes through cap 14 and is provided with a closure plug 54 at its outer end.

In order to obtain a sample of a flowing fluid, solenoid valve 44 is closed, plug 54 is removed from filler tube 52, and chamber 24 is filled with water or other appropriate fluid through filler tube 52. When the chamber is entirely full, plug 54 is reinserted into filler tube 52. The water assures that inflatable bag 20 is deflated. The isokinetic fluid sampler is then placed in the flowing fluid stream at the location from which a sample is desired. When sampling in a river or other body of flowing water, the sampler may be lowered by a cable to the desired sampling point. An electrical conductor within that cable permits control of solenoid valve 44. When the sampler is properly positioned, solenoid valve 44 is opened, and the flowing stream causes propeller 50 to rotate, driving pump 46. The water from within chamber 24 is pumped out exhaust port 40. Since chamber 24 is completely sealed, the flowing fluid is drawn into inlet tube 22, as indicated by arrow 23, to inflate bag 20, replacing the exhausted water. Propeller 50 is driven by the flowing fluid, pump 46 exhausts water from chamber 24 at a rate proportional to the flow rate of the flowing fluid, and the proportionality is based on the ratio of the internal diameters of outlet tube 38 and inlet tube 22 so that the sample enters inlet tube 22 and chamber 24 with the same flow rate as the flow stream. Consequently, the sample is obtained isokinetically. Further, since pump 46 is not in inlet tube 22, the sample is not contaminated by the pump.

Once the desired sample is obtained, solenoid valve 44 is closed, and the sampler is removed from the flowing stream. Latches 16 are opened, and the flexible bag 20, with the fluid sample within it, is removed from the end of inlet tube 22, providing the desired sample.

If desired, solenoid valve 44 can be open as the isokinetic fluid sampler is lowered into the flow stream so as to obtain a depth-averaged sample.

Figure 3:
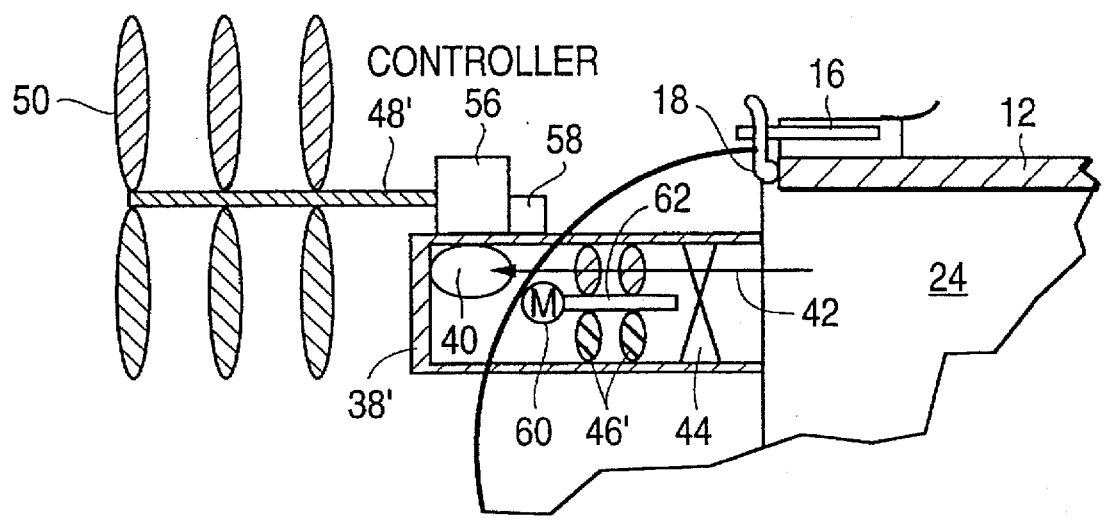
FIG. 3 is a fragmentary sectional view depicting an alternative embodiment of a pump and pump control suitable for incorporation in a fluid sampler in accordance with the present invention.

FIG. 3 depicts an alternative form of a pump which can be utilized with the fluid sampler. In the pump of FIG. 3, propeller 50 is connected by shaft 48' to controller 56 which is connected by cable 58 to motor 60. The shaft 62 of pump 46' is driven by motor 60. Propeller 50 provides controller 56 with an indication of the flow rate of the flowing stream, and in response controller 56 controls the speed at which motor 60 operates so that pump 46' pumps the water from chamber 24 at a rate proportional to the flow rate of the flowing fluid, just as in the embodiment of FIG. 1. Controller 56 can be controlled by signals in an electrical conductor within the cable by which the sampler is lowered into the flow stream, just as is solenoid valve 44.

Whereas in the embodiment of FIG. 1, propeller 50 serves as a flow impeller to power pump 46 at a rate to cause the water or other fluid to be exhausted from chamber 24 at an exhaust rate proportional to the flow rate of the flowing stream, in the embodiment of FIG. 3 propeller 50 serves as a flow rate sensor to provide controller 56 with a signal indicative of the flow rate of the flowing fluid.

The fluid controlled isokinetic fluid sampler of the present invention can be operated at any depth, even below the 17 foot depth of many existing samplers. Further, because chamber 24 contains no air, the vertical transit rate of the sampler is not limited by the compression rate of air as are many existing samplers. The absence of air in the sampler also eliminates any need for a heavy housing or harness to provide stability. Additionally, the fluid sampler of the present invention can obtain samples even in flow streams of low velocity. In extremely low velocity flow streams, the motor driven pump of FIG. 3 can be utilized to assure obtaining the sample isokinetically. Since the pump and valves are separated from the sample inlet path, the sample is not contaminated by these components. The sampler can be readily and quickly reused in the field by simply unlatching the cap from the housing and removing bag 20 containing the sample. If desired, inlet tube 22 can be designed to be easily removed from cap 14 and the more laborious cleaning of inlet tube 22 can be deferred until the sampling is completed, and it is not necessary to clean the sampler inlet tube in the field.

The isokinetic fluid sampler can be used to obtain samples of flowing gases, as well as flowing liquids, if desired. Thus, for example, vehicle exhaust gas might be sampled. However, it is usually not necessary that flowing gases be sampled isokinetically. If desired, housing 12 can be made of a transparent material such as plexiglass to permit viewing of inflatable bag 20 as soon as the sampler is removed from the flow stream.

Although the present invention has been described with reference to preferred embodiments, various substitutions, rearrangements, and alterations can be made and still the result would be within the scope of the invention.

What is claimed is:

1. A fluid controlled isokinetic fluid sampler for obtaining a sample of a flowing fluid, said fluid sampler comprising:
   a fluid tight container adapted to be filled with liquid;
   an inflatable bag within said container and in fluid communication with the exterior of said container;
   means for withdrawing liquid from said container at a flow rate proportional to the flow rate of the flowing fluid to cause a sample of the flowing fluid to be drawn into said inflatable bag at a rate equal to the flow rate of the flowing fluid, to inflate said bag within said container so as to replace the liquid withdrawn from the container.

2. A fluid controlled isokinetic fluid sampler as claimed in claim 1, wherein said inflatable bag includes an inlet tube communicating the interior of said bag with the exterior of said container; said fluid sampler further comprising an outlet tube connected to said container, a pump for pumping the liquid from the container through said outlet tube and to the exterior of said container, and means for driving said pump at a speed to withdraw the liquid from the container at a rate proportional to the flow rate of the flowing fluid, wherein the ratio of the flow rate of the liquid pumped through said outlet tube to the flow rate of the flowing fluid is substantially equal to the ratio of the interior diameter of said inlet tube to the interior diameter of said outlet tube.

3. A fluid controlled isokinetic fluid sampler for obtaining a sample of a flowing fluid, said fluid sampler comprising:
   a hollow closed housing adapted to hold a liquid;

an outlet tube communicating the interior of said housing with the exterior of said housing;

a pump within said outlet tube for pumping the liquid from within said housing through said outlet tube to the exterior of said housing;

an inflatable bag within said housing;

an inlet tube for drawing a sample of the flowing fluid from the exterior of said housing into said inflatable bag to inflate said bag within said housing as the liquid is pumped from within said housing; and control means responsive to the flowing fluid for causing said pump to pump the liquid from within said housing through said outlet tube to the exterior of said housing at a flow rate proportional to the flow rate of the flowing fluid, drawing a sample of the flowing fluid through said inlet tube into said inflatable bag to inflate said bag within said housing.

4. A fluid controlled isokinetic fluid sampler as claimed in claim 3, wherein said control means comprises a flow impeller adapted to be driven by the flowing fluid.

5. A fluid controlled isokinetic fluid sampler as claimed in claim 3, wherein said control means comprises a motor for driving said pump and a flow rate sensor for controlling the speed at which said pump is driven by said motor.

6. A fluid controlled isokinetic fluid sampler as claimed in claim 5, wherein said flow rate sensor is a propeller.

7. A fluid controlled isokinetic fluid sampler as claimed in claim 3, wherein said inlet tube extends from said housing further than said outlet tube extends from said housing.

8. A fluid controlled isokinetic fluid sampler as claimed in claim 3, further comprising a filler tube for filling said housing with the liquid.

9. A fluid controlled isokinetic fluid sampler as claimed in claim 3, further comprising a solenoid valve in said outlet tube for blocking flow of the liquid through said outlet tube and operable to permit flow of the liquid through said outlet tube when a sample is to be drawn into said inflatable bag.

10. A fluid controlled isokinetic fluid sampler as claimed in claim 3, wherein the ratio of the flow rate of the liquid pumped through said outlet tube to the flow rate of the flowing fluid is substantially equal the ratio of the interior diameter of said inlet tube to the interior diameter of said outlet tube.

\* \* \* \* \*